(12) United States Patent
Govari et al.

(10) Patent No.: US 12,023,106 B2
(45) Date of Patent: Jul. 2, 2024

(54) VIRTUAL REALITY 3D EYE-INSPECTION BY COMBINING IMAGES FROM POSITION-TRACKED OPTICAL VISUALIZATION MODALITIES

(71) Applicant: JOHNSON & JOHNSON SURGICAL VISION, INC., Irvine, CA (US)

(72) Inventors: Assaf Govari, Haifa (IL); Vadim Gliner, Haifa (IL); Andres Claudio Altmann, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 844 days.

(21) Appl. No.: 17/068,084

(22) Filed: Oct. 12, 2020

(65) Prior Publication Data
US 2022/0110691 A1    Apr. 14, 2022

(51) Int. Cl.
*A61B 34/20* (2016.01)
*A61B 3/13* (2006.01)
(Continued)

(52) U.S. Cl.
CPC ............ *A61B 34/20* (2016.02); *A61B 6/03* (2013.01); *A61B 34/35* (2016.02); *A61B 34/70* (2016.02);
(Continued)

(58) Field of Classification Search
CPC ........ A61B 2090/365; A61B 2090/367; A61B 3/13
See application file for complete search history.

(56) References Cited

U.S. PATENT DOCUMENTS

| 4,818,110 A | 4/1989 | Davidson |
| 5,345,087 A | 9/1994 | Luber et al. |

(Continued)

FOREIGN PATENT DOCUMENTS

| CN | 109276265 A | 1/2019 |
| DE | 102013013492 A1 | 2/2015 |

(Continued)

OTHER PUBLICATIONS

Draelos M., et al., "Real-time Visualization and Interaction With Static and Live Optical Coherence Tomography Volumes in Immersive Virtual Reality," Biomedical Optics Express, May 2018, vol. 9(6), pp. 2825-2843.

(Continued)

*Primary Examiner* — Kevin Ky
(74) *Attorney, Agent, or Firm* — Johnson & Johnson Surgical Vision, Inc.

(57) ABSTRACT

A medical visualization apparatus includes two or more imaging devices, two or more robotic arms, multiple magnetic sensors coupled with the imaging devices, and a processor. The two or more imaging devices are configured to acquire images of an organ of a patient. The two or more robotic arms are configured to move the respective imaging devices. The multiple magnetic sensors are configured to output, in response to a magnetic field of a position tracking system, signals indicative of positions and viewing directions of the imaging devices. The processor is configured to estimate a position and a viewing direction of each of the imaging devices based on the signals, and, using the estimated positions and viewing directions, combine the images of the organ acquired by the imaging devices into a virtual reality (VR) image of the organ, and present the VR image to a user on a VR viewer.

16 Claims, 3 Drawing Sheets

(51) Int. Cl.
  *A61B 6/03* (2006.01)
  *A61B 34/00* (2016.01)
  *A61B 34/35* (2016.01)
  *A61B 90/00* (2016.01)

(52) U.S. Cl.
  CPC ............ *A61B 90/361* (2016.02); *A61B 90/37* (2016.02); *A61B 3/13* (2013.01); *A61B 2034/2051* (2016.02); *A61B 2034/2065* (2016.02); *A61B 2090/365* (2016.02); *A61B 2090/367* (2016.02); *A61B 2090/3735* (2016.02)

(56) References Cited

U.S. PATENT DOCUMENTS

| | | | |
|---|---|---|---|
| 5,391,199 | A | 2/1995 | Ben-Haim |
| 6,006,126 | A | 12/1999 | Cosman |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 8,049,873 | B2 | 11/2011 | Hauger et al. |
| 8,379,218 | B2 | 2/2013 | Deck et al. |
| 9,844,321 | B1 | 12/2017 | Ekvall et al. |
| 10,258,426 | B2 | 4/2019 | Silva et al. |
| 10,303,940 | B2 | 5/2019 | Zhang et al. |
| 10,517,760 | B2 | 12/2019 | Berlin |
| 10,638,080 | B2 | 4/2020 | Ovchinnikov et al. |
| 11,906,745 | B1* | 2/2024 | Zhao ................ G06F 3/011 |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2004/0106916 | A1* | 6/2004 | Quaid ................ A61B 34/71 606/1 |
| 2004/0257360 | A1 | 12/2004 | Sieckmann |
| 2008/0204864 | A1 | 8/2008 | Sander |
| 2008/0287781 | A1* | 11/2008 | Revie ................ A61B 90/36 382/131 |
| 2009/0278791 | A1* | 11/2009 | Slycke ................ A61B 5/1114 345/156 |
| 2013/0293888 | A1* | 11/2013 | Zhao ................ G02B 27/283 359/490.02 |
| 2014/0160264 | A1 | 6/2014 | Taylor et al. |
| 2014/0179997 | A1 | 6/2014 | Von Grunberg et al. |
| 2014/0296694 | A1* | 10/2014 | Jaworski ................ A61B 8/5246 600/424 |
| 2016/0008169 | A1 | 1/2016 | Yu |
| 2016/0183779 | A1 | 6/2016 | Ren et al. |
| 2016/0228204 | A1* | 8/2016 | Quaid ................ A61B 34/10 |
| 2016/0327806 | A1* | 11/2016 | Kasamatsu ............ G02B 27/646 |
| 2017/0007450 | A1 | 1/2017 | Samee et al. |
| 2017/0078651 | A1 | 3/2017 | Russell |
| 2017/0280989 | A1 | 10/2017 | Heeren |
| 2018/0008232 | A1* | 1/2018 | Mine ................ A61B 8/14 |
| 2018/0116728 | A1* | 5/2018 | Lang ................ A61B 17/155 |
| 2018/0220103 | A1* | 8/2018 | Wang ................ G01S 19/13 |
| 2018/0341323 | A1 | 11/2018 | Mate et al. |
| 2018/0368656 | A1* | 12/2018 | Austin ................ A61B 1/045 |
| 2019/0000314 | A1 | 1/2019 | Awdeh |
| 2019/0005709 | A1 | 1/2019 | Kim et al. |
| 2019/0101757 | A1 | 4/2019 | Martinez et al. |
| 2019/0133289 | A1 | 5/2019 | Rocha et al. |
| 2019/0298448 | A1 | 10/2019 | Kerbage et al. |
| 2019/0380566 | A1 | 12/2019 | Charles et al. |
| 2020/0059640 | A1 | 2/2020 | Browd et al. |
| 2020/0069218 | A1 | 3/2020 | Gliner et al. |
| 2020/0107701 | A1* | 4/2020 | Gliner ................ A61B 1/00158 |
| 2020/0188173 | A1 | 6/2020 | Berlin |
| 2021/0088688 | A1* | 3/2021 | Chapman ............ G05B 13/048 |
| 2021/0137634 | A1* | 5/2021 | Lang ................ A61B 5/113 |
| 2021/0186619 | A1* | 6/2021 | Levi ................ A61B 34/10 |
| 2021/0186620 | A1* | 6/2021 | Gliner ................ A61B 34/25 |
| 2021/0192759 | A1* | 6/2021 | Lang ................ A61B 34/20 |
| 2021/0281802 | A1 | 9/2021 | Kirisken |
| 2021/0325649 | A1 | 10/2021 | Segev et al. |
| 2022/0103744 | A1* | 3/2022 | Hsu ................ G03B 30/00 |
| 2022/0110691 | A1* | 4/2022 | Govari ................ A61B 3/0025 |
| 2022/0122239 | A1 | 4/2022 | Govari et al. |
| 2022/0387128 | A1* | 12/2022 | Bail ................ H04N 13/279 |
| 2023/0210604 | A1* | 7/2023 | Berman ................ A61B 6/12 378/177 |

FOREIGN PATENT DOCUMENTS

| | | |
|---|---|---|
| EP | 0697611 A2 | 2/1996 |
| EP | 3387984 B1 | 4/2020 |
| WO | 9605768 A1 | 2/1996 |
| WO | 2017066373 A1 | 4/2017 |
| WO | 2018216156 A1 | 11/2018 |
| WO | 2019148154 A1 | 8/2019 |

OTHER PUBLICATIONS

Nam Hyun Cho et al., In vivo imaging of middle-ear and inner-ear microstructures of a mouse guided by SD-OCT combined with a surgical microscope, Optics Express, Apr. 21, 2014, vol. 22, No. 8, DOI:10.1364/OE.22.008985, Optics Express 8987.

Cesare Giorgi et al., (1995) Robot-Assisted Microscope for Neurosurgery, Journal of Image Guided Surgery, 1:3, 158-163, no data available.

Raabid Hussain et al., Video-based augmented reality combining CT-scan and instrument position data to microscope view in middle ear surgery, Scientific Reports, (2020), www.nature.com/scientificreports, no data available.

* cited by examiner

VIRTUAL REALITY 3D EYE-INSPECTION BY COMBINING IMAGES FROM POSITION-TRACKED OPTICAL VISUALIZATION MODALITIES

FIELD OF THE INVENTION

The present invention relates generally to medical position-trackable robotic organ-examination systems, and particularly to visual inspection of an eye using position-trackable robotic systems employing virtual reality.

BACKGROUND OF THE INVENTION

An eye is a complex optical system which collects light from the surrounding environment, regulates its intensity through a diaphragm, focuses it through an adjustable assembly of lenses to form an image, converts this image into a set of electrical signals, and transmits these signals to the brain through complex neural pathways that connect the eye via the optic nerve to the visual cortex and other areas of the brain. To this end, the eye consists of a multi layered 3D eyeball made of various types of tissue, with each tissue having its unique material characteristics and features, including low contrast patterns located at different sections of the eye and are hard to visualize, such as the lens, blood vessels and nerves.

Various techniques to visualize a volume of eye, such as for eye surgery planning, were proposed in the patent literature. For example, U.S. Pat. No. 10,517,760 describes systems and methods for aiding a surgeon to perform a surgical procedure on an eye. Exemplary systems include an optical microscope for the surgeon to view the eye with a microscope image during the procedure; an optical coherence tomography (OCT) apparatus configured to perform an OCT scan of a target location in the target tissue region during the procedure; and an image processing apparatus configured to generate an augmented image by overlaying an OCT image of target location and a graphical visual element identifying the locations, wherein the graphical visual element is registered with the microscope image to aid the surgeon in advancing a distal end of the elongate probe to the target location.

As another example, U.S. Patent Application Publication 2014/0160264 describes an augmented field of view imaging system that includes a microscope, an image sensor system arranged to receive images of a plurality of fields of view from the microscope as the microscope is moved across an object being viewed and to provide corresponding image signals, an image processing and data storage system configured to communicate with the image sensor system to receive the image signals and to provide augmented image signals, and at least one of an image injection system or an image display system configured to communicate with the image processing and data storage system to receive the augmented image signals and display an augmented field of view image. The image processing and data storage system is configured to track the plurality of fields of view in real time and register the plurality of fields of view to calculate a mosaic image. The augmented image signals from the image processing and data storage system provide the augmented image such that a live field of view from the microscope is composited with the mosaic image.

SUMMARY OF THE INVENTION

An embodiment of the present invention that is described hereinafter provides a medical visualization apparatus including two or more imaging devices, two or more robotic arms, multiple magnetic sensors, and a processor. The two or more imaging devices are configured to acquire images of an organ of a patient. The two or more robotic arms are configured to move the respective imaging devices. The multiple magnetic sensors, which are coupled with the two or more imaging devices, are configured to output, in response to a magnetic field of a position tracking system, signals indicative of positions and viewing directions of the two or more imaging devices. The processor is configured to: (a) estimate a position and a viewing direction of each of the imaging devices based on the signals, and b) using the estimated position and viewing direction of each of the imaging devices, combine the images of the organ acquired by the two or more imaging devices into a virtual reality image of the organ, and present the virtual reality image to a user on a virtual reality viewing device.

In some embodiments, at least one of the two or more imaging devices includes one or more selectable wavelength filters.

In some embodiments, each of the two or more imaging devices include at least one of a 3D microscope, a thermal camera, and an OCT device.

In an embodiment, the two or more imaging devices include at least two microscope objectives.

In some embodiments, the processor is configured to move at least one of the two or more robotic arms according to a user request specifying a gazing direction.

In other embodiments, the processor is configured to combine the images independently of any coordinate-system registration between the two or more imaging devices.

In an embodiment, at least one of the multiple magnetic sensors is configured to output, in response to the magnetic field, one or more signals indicative of a roll angle of an imaging device about the estimated viewing direction of at least one of the two or more imaging devices, and wherein the processor is further configured to estimate the roll angle based on the one or more signals.

In another embodiment, wherein at least one of the two or more imaging devices include a light polarizer, and wherein the processor is configured to adjust the light polarizer by adjusting the roll angle.

There is additionally provides, in accordance with another embodiment of the present invention, a medical visualization method including acquiring images of an organ of a patient using two or more imaging devices. The imaging devices are moved using two or more respective robotic arms. In response to a magnetic field of a position tracking system, signals are generated, that are indicative of positions and viewing directions of the two or more imaging devices, using multiple magnetic sensors which are coupled with the two or more imaging devices. A position and a viewing direction of each of the imaging devices are estimated based on the signals. Using the estimated position and viewing direction of each of the imaging devices, the images of the organ acquired by the two or more imaging devices are combined into a virtual reality image of the organ, and the virtual reality image is presented to a user on a virtual reality viewing device.

The present invention will be more fully understood from the following detailed description of the embodiments thereof, taken together with the drawings in which:

DETAILED DESCRIPTION OF EMBODIMENTS

Overview

Figure 1:
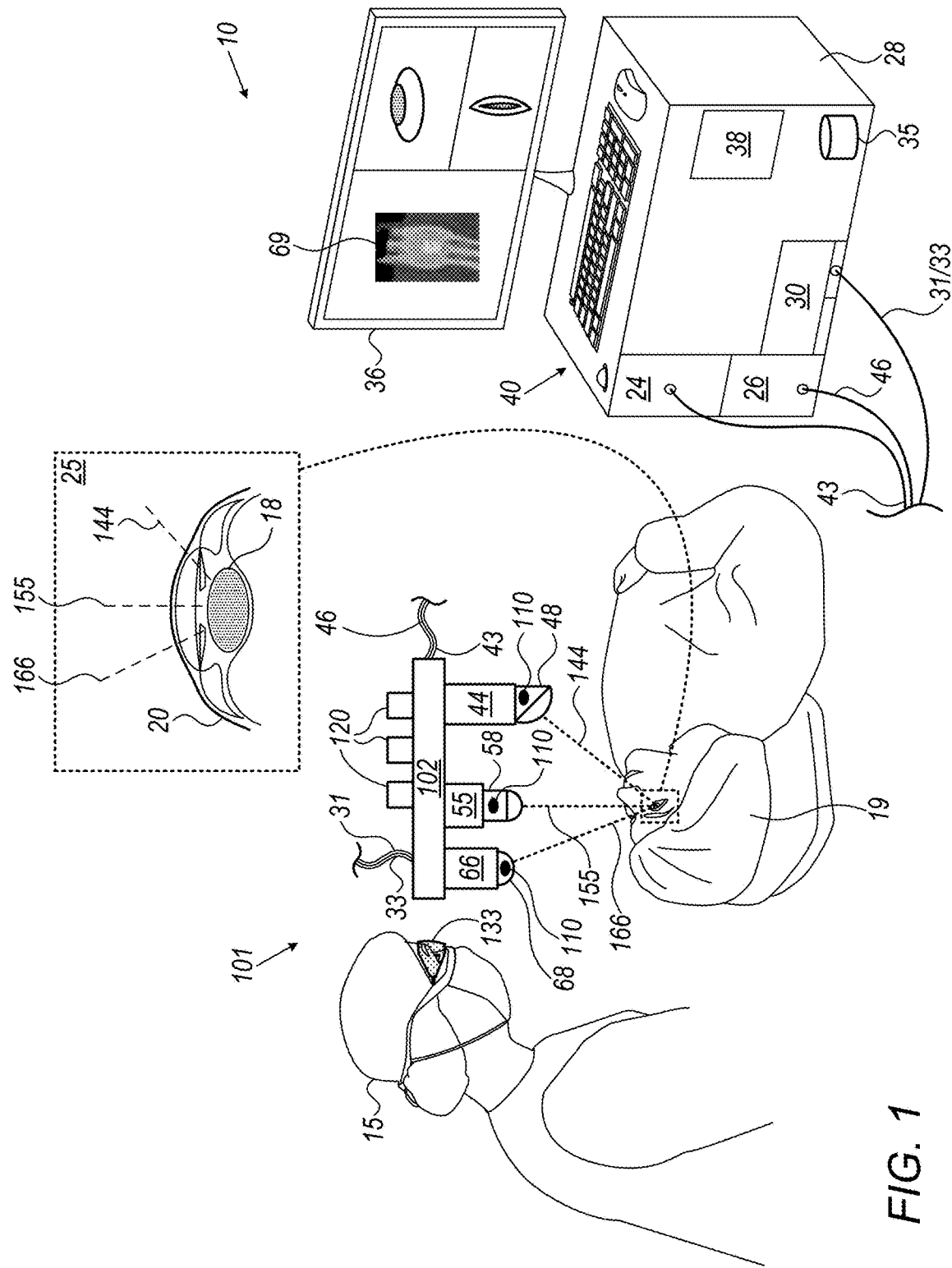
FIG. 1 is a schematic, pictorial view of an eye-inspection system comprising position-trackable robot-mounted eye-imaging devices and virtual-reality eyeglasses, in accordance with an embodiment of the present invention.

Embodiments of the present invention that are described hereinafter combine images of an organ (e.g., an eye) being diagnosed and/or treated (e.g., surgically), that are taken from multiple optical imaging devices of one or more imaging modalities, that can be mounted on robotic arms, such as OCT images and 3D digital microscope images. The position and the viewing direction of each of the optical imaging devices are tracked with a magnetic tracking system, by tracking multiple magnetic sensors coupled to the imaging devices, and the processor combines the produced images into a multi-layered 3D image of the eye. The 3D image is then transmitted to a virtual reality viewing device, such as virtual reality eyeglasses, worn by the physician.

The physician can select the gaze direction to view the eye, for instance by using an add-on for the finger to act as a virtual pointer. Using the tracked position and direction, a processor aligns all images and compensates for motion without a need for careful registration of different frames of references of the different modalities that may be moved during the process intentionally (by the robotic arms) or unintentionally (for example by actions of personnel in a sophisticated surgical theater setting).

In some embodiments, at least some of the optical imaging devices, such as the 3D digital microscope, are held by robot arms which are tracked by the magnetic tracking system. The robot arm is manipulated so that multiple images (e.g., microscope images and/or OCT images) are acquired from different viewing directions. The physician is able to select a particular viewing direction, for example of the 3D microscope, and the images are then presented to the physician in a virtual reality device by, for example, toggling the two images between the physician's left and right eyes.

The optical imaging modalities may have numerous dissimilar characteristics, such as, for example, different focal lengths, different fields of view, and/or different operating speeds and optical wavelengths. At least some of the optical imaging devices may comprise, for example miniature cameras such as a fundus camera. In some embodiments, at least some of the optical imaging devices comprise one or more filters, which allow the physician to select a wavelength range, e.g. the visible spectrum, near- or far-infrared, or thermal wavelengths, for viewing the eye.

In some embodiments, at least one of the multiple magnetic sensors is configured to output, in response to a magnetic field of the position tracking system, signals indicative of a roll angle of an imaging device, and the processor is configured to, based on the signals, estimate the roll angle about the estimated direction. In this embodiment, two or more imaging devices may comprise one or more light polarizers that the processor adjusts by adjusting the roll angle.

The optical imaging devices (e.g., cameras) are distributed such that their images cover a substantial portion of the eye. The optical imaging devices may be standalone systems or may be attached to other system elements, such as to a respective objective of a microscope.

The OCT images are tomographic images, i.e., slices, that are orthogonal to the optical axis of an OCT assembly. The physician can select from which part of the optical axis the OCT image is to be used in the virtual reality device.

In some embodiments, a microscope objective is mounted on a robotic arm with six degrees of freedom, which is tracked with a magnetic tracking system. The image of the object acquired by the objective is transferred to virtual reality eyeglasses worn by a user, who is then able to operate the robotic arm so as to select a direction of observation of the objective. The combination of the robotic microscope coupled to virtual reality eyeglasses gives much greater freedom of viewing direction than is possible with a standard microscope.

A further use of the robotic arm-mounted microscope may be to build a 3D image of the viewed eye. In this case the objective is assumed to have a small depth of field. The objective is moved along its optical axis, and is used to capture images of elements of the object that are in sharp focus. These images are used to build a 3D image of the object.

In another embodiment, two microscopes mounted on robotic arms are used (possibly with one or more additional optical imaging modalities), each robotic arm having six degrees of freedom, to which a microscope objective is attached. The positions, viewing directions, and, optionally, roll-angles, of the objectives are magnetically tracked using a magnetic tracking system. Each image of the viewed object, acquired by a respective objective, is transferred to virtual reality eyeglasses worn by a user, and the separate images are presented to the user's left and right eye. The user views the separate images as in a standard digital 3D microscope.

However, the robotic arms of the invention enable the user to view the object from a much wider range of viewing directions compared to the standard 3D digital microscope. In addition, the user is able to change the separation of the objectives at will, so as to enhance or reduce the 3D effect.

Using the disclosed virtual 3D optical imaging techniques that include augmenting images from multiple optical imaging modalities that are position tracked into a 3D virtual reality image, may allow the performance of eye surgeries more easily, more effectively, and with fewer hazards.

System Description

FIG. 1 is a schematic, pictorial view of an eye-inspection system 10 comprising position-trackable robot-mounted eye imaging devices (48, 58, 68) and virtual reality eyeglasses 133, in accordance with an embodiment of the present invention.

System 10 has robotic arms 44, 55 and 66 mounted on a fixed base 102 (e.g., suspended from a ceiling). Imaging device 48 may have a camera with an optical imaging axis 144 that is coupled with robotic arm 44; imaging device 58 may include an OCT, including an objective with an optical imaging axis 155 and a camera, that is coupled to robotic arm 55; and imaging device 68 may have a 3D digital microscope with an optical imaging axis 166 with a variable focus length on axis 166 that is coupled with robotic arm 66.

The robotic arms are controlled by a processor 38 that may vary directions 144/155/166 and/or depth of imaging along direction 144/155/166, according to a gaze direction selected by the physician to view the eye, for instance by using a pointing device such as a mouse or a trackball of a user interface 40, or by moving a finger add-on (not shown) to act as a virtual pointer.

As inset 25 shows, directions 144/155/166 are aligned so as to provide an unobstructed optical path for each of the imaging devices (48/58/68) to view a lens 18 of an eye 20 of a patient 19.

In an embodiment, system 10 is equipped with robotic arms (44, 55, 66) having six degrees of freedom, though the number of degrees of freedom may vary with design, typically with a minimum of two or three (e.g., to point at a solid angle direction (2), and vary depth of focus (1)).

During eye inspection, one or more of robotic arms 44/55/66 move the imaging devices (48/58/68) according to commands from processor 38 communicated via cables 31/43/46 running between a console 28 and base 102, where cable 31 is further used to convey signals from imaging device 48 having a thermal camera to processor 38. Cable 43 is further used to convey signals from the camera behind imaging device 58 having a camera objective to OCT subsystem 24, and cable 46 is further used to convey signals from imaging device 68 having a 3D digital microscope to a 3D digital microscope subsystem 26.

In the shown embodiment, system 10 comprises a magnetic-sensing subsystem 101 to estimate positions and directions of the imaging devices (48/58/68). To this end, patient 19 is placed in a magnetic field generated by a pad containing magnetic field generator coils 120, which are driven by unit 30 via a cable 33. The magnetic fields generated by coils 120 generate position signals in magnetic sensors 110, each coupled to imaging devices (48/58/68). The signals from each sensor 110 are then provided, as corresponding electrical inputs, to processor 38 to calculate the separate position and direction of each of imaging devices (48/58/68).

The method of position sensing using external magnetic fields and magnetic sensor is implemented in various medical applications, for example, in the CARTO™ system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In the shown embodiment, imaging device 48 having a thermal camera captures a thermal image of lens 18 in real time. The captured image 69 is displayed on a display 36. Beyond its possible use in diagnostics, the displayed thermal image enables physician 15 to monitor temperature and prevent thermal hazard to eye 20 during surgery (e.g., laser or focused ultrasound, neither of which are shown).

Processor 38 presents other results of a diagnostic and/or therapeutic procedure on display 36. As noted above, processor 38 may receive user-based commands via a user interface 40. User interface 40 may be combined with a touchscreen graphical user interface of display 36.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements, which are omitted for clarity of presentation. For example, physician 15 may hold a control handle which can, for example, command processor 38. Physician 15 may use surgical tools and/or apply medications, which are also not shown in order to maintain clarity and simplicity of presentation.

Figure 2:
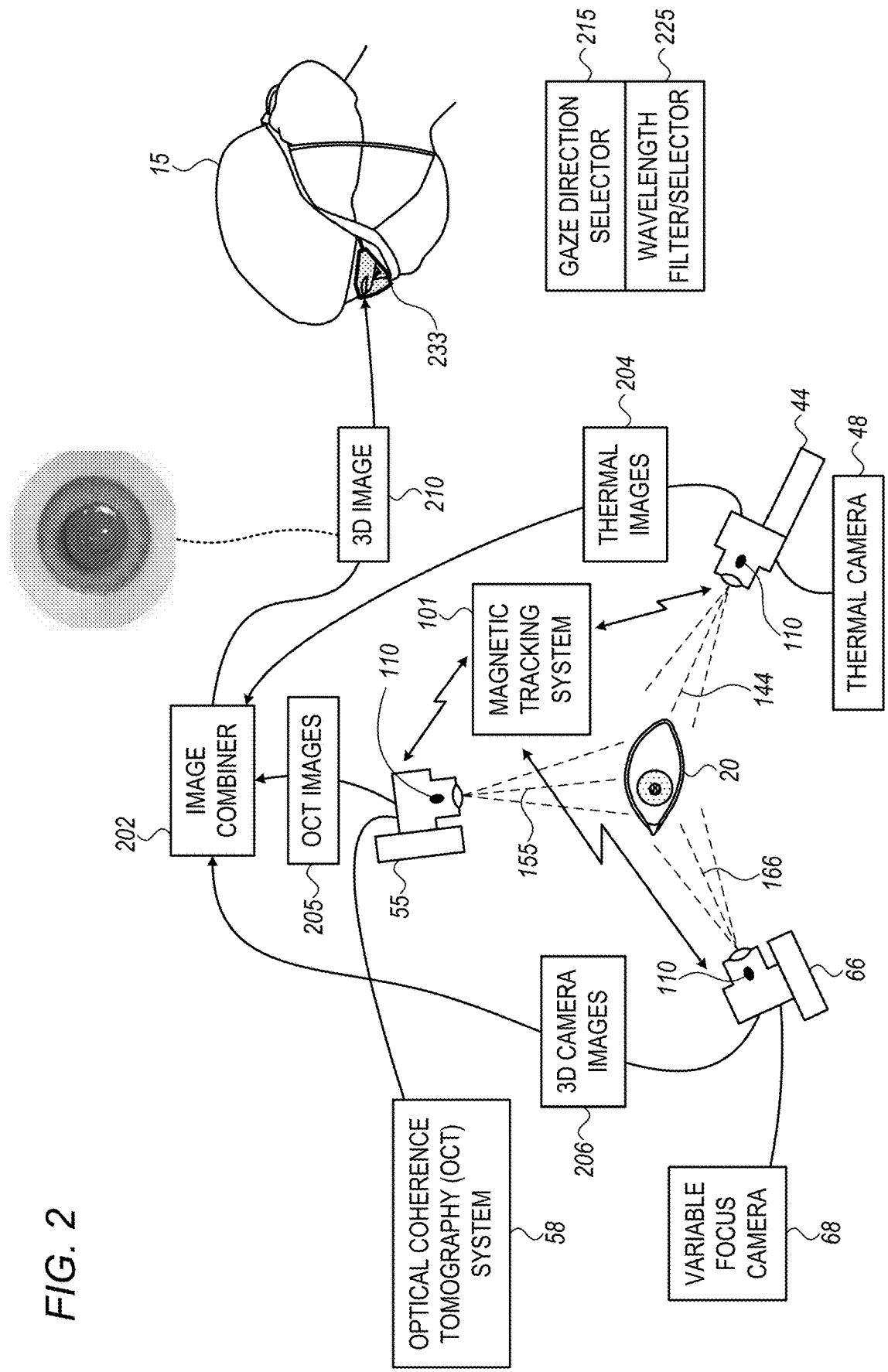
FIG. 2 is a schematic, pictorial view of the position-trackable robot-mounted eye-imaging devices of the eye inspection system of FIG. 1, in accordance with an embodiment of the present invention.

Virtual Reality 3D Eye Inspection by Combining Images from Position-Tracked Optical Imaging Modalities FIG. 2 is a schematic, pictorial view of the position-trackable robotic arms 44/55/66 mounted eye imaging devices 48/58/68 of eye inspection system 10 of FIG. 1, in accordance with an embodiment of the present invention.

As seen, imaging devices 48/58/68 are arranged in space to have unobstructed views 144/155/166 of eye 20, and the imaging devices can be maneuvered by respective robotic arms 44/55/66 so that the arrangement of the different acquisitions (positions and directions) can be adjusted by processor 38, as directed by physician 15 by selecting a gaze direction using a gaze direction selector 215 to view the eye, to generate a combined 3D image 210 of eye 20 that physician 15 views on virtual reality eyeglasses 233. Moreover, combined 3D image 210 may present the physician information related to a wavelength range selected via a wavelength filter/selector 225 for viewing the eye, e.g. the visible spectrum, near- or far-infrared, or thermal wavelengths.

To this end, using the tracked position and viewing direction of imaging devices 48/58/68, obtained by magnetic tracking system 101 using sensors 110, processor 38 aligns all images (thermal images 204, OCT images 205, and 3D camera images 206). Processor 38 compensates for motion of imaging devices 48/58/68 without a need for registration of different frames of reference of the different modalities (devices), that may be moved during the procedure, either intentionally (by the robotic arms) or unintentionally, for example, by actions of personnel in a sophisticated surgical theater setting.

In the shown embodiment, an image combiner module 202 of processor 38 combines thermal images 204, OCT images 205 and 3D microscope camera images 206 into 3D image 210, the microscope having a variable focal length to enable 3D image creation by scanning a moving object plane along direction 166 (the plane normal to direction 166).

Physician 15 can receive more information on virtual reality eyeglasses 233, by, for example, varying wavelength filter types of the 3D digital microscope of imaging device 68 and/or the OCT device of imaging device 58 and/or the thermal camera of imaging device 48. Physician 15 can change filters and/or gazing direction using controls specified in FIG. 1. Using additional controls physician 15 may choose to switch between combined image 210 to images from any of one or more of the modalities.

The example unit shown in FIG. 2 is chosen purely for the sake of conceptual clarity. For example, combined image 210 may be generated from more than three imaging modalities.

Virtual Reality 3D Microscope

Figure 3:
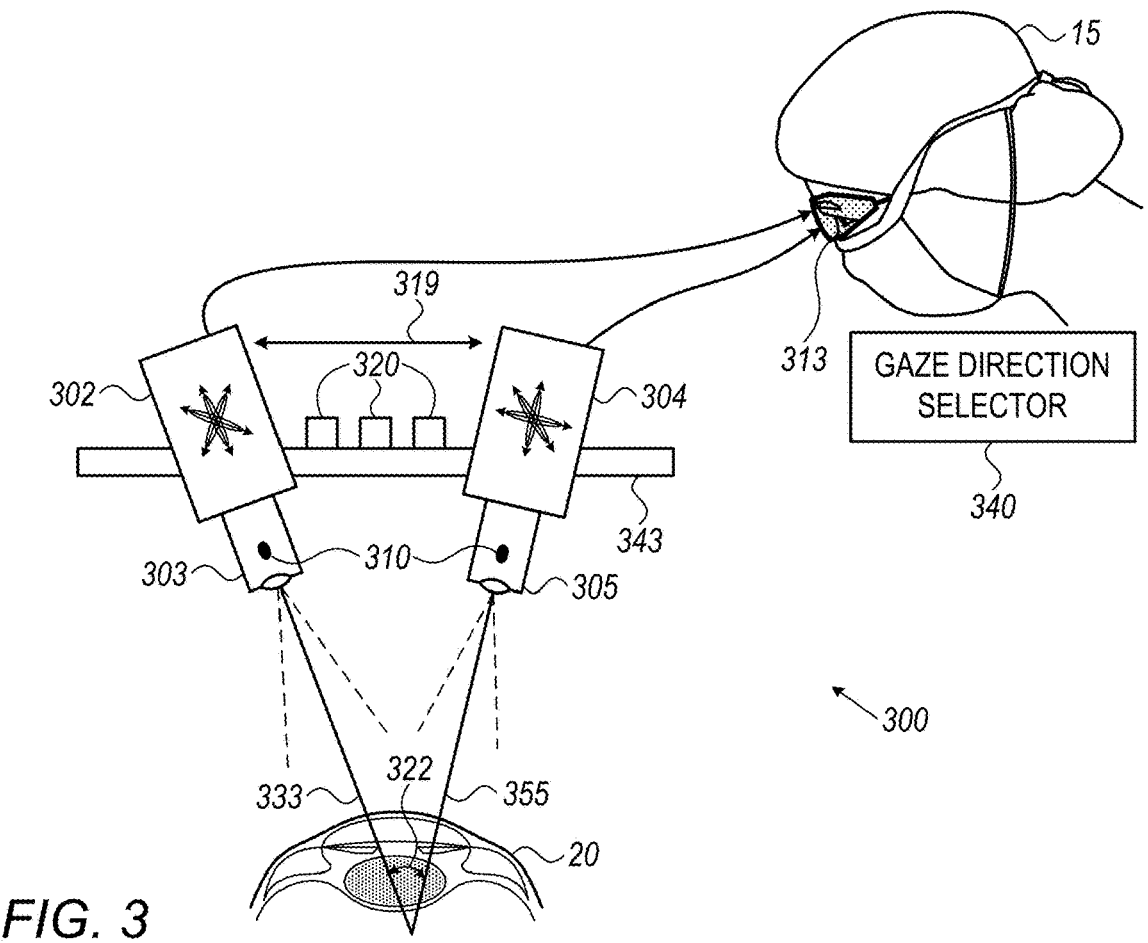
FIG. 3 is a schematic, pictorial view of a position-trackable robotic eye inspection system, in accordance with another embodiment of the present invention.

FIG. 3 is a schematic, pictorial view of a position-trackable robotic eye-inspection system 300, in accordance with another embodiment of the present invention. System 300 comprises two focus cameras (303, 305) each including a microscope objective coupled to respective robotic arms (302, 304) that are coupled with a stationary rail 343. The robotic arms have a separation 319 between them, which can be adjusted, for example, by using a motorized assembly on a rail (not shown). The user is able to change the separation of the objectives in order to receive an enhanced or reduced 3D effect at will, depending on the angle 322 between the viewing directions (333, 355) of the objectives.

The two robotic arms each have six degrees of freedom of motion, with the positions and viewing directions of the objectives magnetically tracked using a magnetic tracking system comprising magnetic field generator coils 320 similar to coils 120 of FIG. 1, and magnetic sensors 310 similar to sensors 110 of FIG. 1.

Each image of the viewed object, acquired by a respective objective, is transferred to virtual reality eyeglasses 313 worn by physician 15, and the separate images are presented to the left and right eye of the physician. The physician views the separate images as in a standard 3D microscope. The robotic arms, when combined with the magnetic tracking, enable the user to view the object (e.g., an eye 20) from a much wider range of viewing directions, depending for example, on selecting a gaze direction via a gaze direction selector 340 (e.g., a direction "into the page" in FIG. 3) to view the eye, compared to the standard microscope.

Method for Using the Position-Trackable Robot Eye Inspection System

Figure 4:
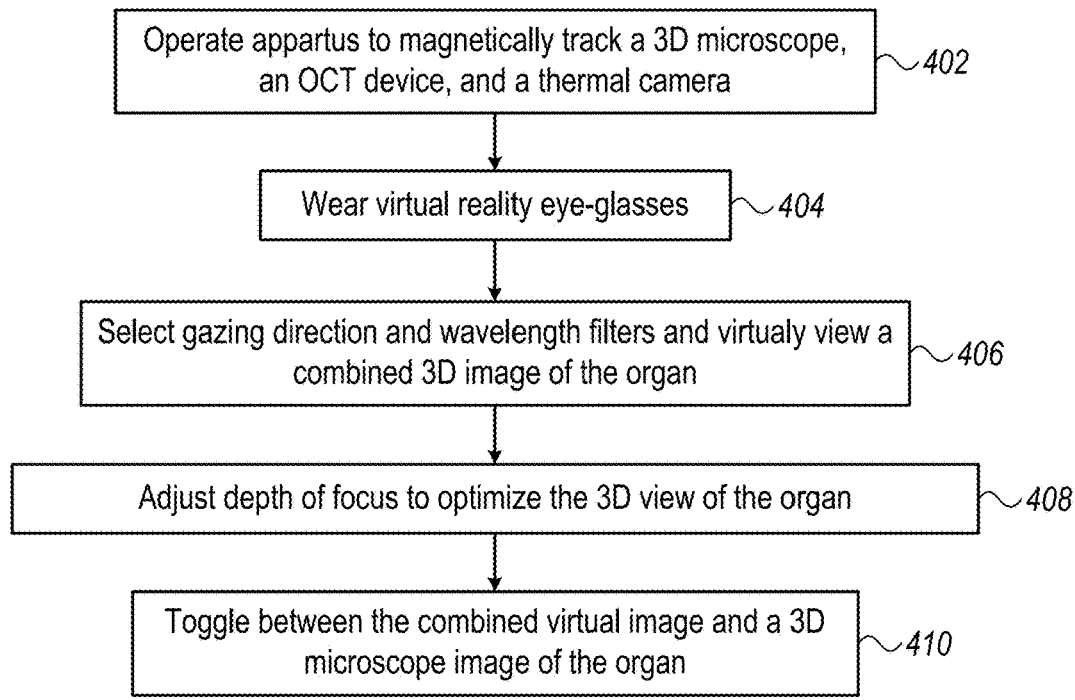
FIG. 4 is a flow chart schematically illustrating a method for using the position-trackable robot eye inspection system of FIG. 1, in accordance with an embodiment of the present invention.

FIG. 4 is a flow chart schematically illustrating a method for using the position-trackable robot eye inspection system of FIG. 1, in accordance with an embodiment of the present invention. The algorithm, according to the presented embodiment, carries out a process that begins with physician 15 operating apparatus 10 (e.g., processor 38) to start tracking the positions and viewing directions of 3D digital microscope of imaging device 68, OCT device of imaging device 58 and thermal camera of imaging device 48, at a magnetic tracking initiation step 402.

Physician 15 then wears virtual reality eyeglasses and verifies the presence of an image screen, at a VR preparatory step 404.

Next, at a setting step 406, the physician selects a gazing direction and wavelength filters to view a combined image of the organ.

At a next 3D view setting step, the physician uses controls, such as from user interface 40, to adjust a depth of focus of 3D microscope of imaging device 68 for a best 3D view the organ.

Finally, using the controls, the physician toggles between views, such as between the combined 3D image and one of the images (e.g., of the 3D microscope) at a view toggling step 410.

The example flow chart shown in FIG. 4 is chosen purely for the sake of conceptual clarity. For example, additional inspection steps, such as noninvasive intra-ocular pressure measurement, may also be performed.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical visualization apparatus, comprising:
two or more imaging devices that are configured to acquire images of an organ of a patient;
two or more robotic arms configured to move the respective two or more imaging devices;
a pad containing one or more magnetic field generator coils to generate a magnetic field of a position tracking system near the patient;
multiple magnetic sensors, at least one magnetic sensor coupled with each of the two or more imaging devices, the multiple magnetic sensors are configured to output, in response to the magnetic field of the position tracking system, signals indicative of positions and viewing directions of the two or more imaging devices; and
a processor, which is configured to:
estimate a position and a viewing direction of each of the two or more imaging devices based on the signals; and
using the estimated position and viewing direction of each of the two or more imaging devices, combine the images of the organ acquired by the two or more imaging devices into a virtual reality image of the organ, and present the virtual reality image to a user on a virtual reality viewing device.

2. The apparatus according to claim 1, wherein at least one of the two or more imaging devices comprises one or more selectable wavelength filters.

3. The apparatus according to claim 1, wherein each of the two or more imaging devices comprise at least one of a 3D microscope, a thermal camera, and an optical coherence tomography (OCT) device.

4. The apparatus according to claim 1, wherein the two or more imaging devices comprise at least two microscope objectives.

5. The apparatus according to claim 1, wherein the processor is configured to move at least one of the two or more robotic arms according to a user request specifying a gazing direction.

6. The apparatus according to claim 1, wherein the processor is configured to combine the images independently of any coordinate-system registration between the two or more imaging devices.

7. The apparatus according to claim 1, wherein at least one of the multiple magnetic sensors is configured to output, in response to the magnetic field, one or more signals indicative of a roll angle of an imaging device about the estimated viewing direction of at least one of the two or more imaging devices, and wherein the processor is further configured to estimate the roll angle based on the one or more signals.

8. The apparatus according to claim 7, wherein at least one of the two or more imaging devices comprise a light polarizer, and wherein the processor is configured to adjust the light polarizer by adjusting the roll angle.

9. A medical visualization method, comprising:
positioning a pad near a patient, wherein the pad comprises one or more magnetic field generator coils configured to generate a magnetic field for a position tracking system;
acquiring images of an organ of a patient using two or more imaging devices;
moving the two or more imaging devices using two or more respective robotic arms;
generating, in response to the magnetic field of the position tracking system, signals indicative of positions and viewing directions of the two or more imaging devices using multiple magnetic sensors, at least one magnetic sensor coupled to each of the two or more imaging devices;
estimating a position and a viewing direction of each of the two or more imaging devices based on the signals; and
using the estimated position and viewing direction of each of the two or more imaging devices, combining the images of the organ acquired by the two or more imaging devices into a virtual reality image of the organ, and presenting the virtual reality image to a user on a virtual reality viewing device.

10. The method according to claim 9, wherein acquiring the images comprises applying one or more selectable wavelength filters in at least one of the two or more imaging devices.

11. The method according to claim 9, wherein each of the two or more imaging devices comprise at least one of a 3D microscope, a thermal camera, and an optical coherence tomography (OCT) device.

12. The method according to claim 9, wherein the two or more imaging devices comprise at least two microscope objectives.

13. The method according to claim 9, wherein moving the two or more imaging devices comprises moving the two or more imaging devices according to a user request specifying a gazing direction.

14. The method according to claim 9, wherein combining the images comprises combining the images independently of any coordinate-system devices registration between the imaging.

15. The method according to claim 9, further comprising generating from at least one of the magnetic sensors, in response to the magnetic field, one or more signals indicative of a roll angle of at least one of the two or more imaging devices about the estimated viewing direction of the at least one of the two or more imaging devices, and estimating the roll angle based on the one or more signals.

16. The method according to claim 15, wherein at least one of the two or more imaging devices further comprise one or more light polarizers; and further comprising adjusting the roll angle of at least one of the two or more imaging devices.

* * * * *